United States Patent [19]

Chastain et al.

[11] Patent Number: 5,294,645
[45] Date of Patent: Mar. 15, 1994

[54] USING MENTH-1-EN-9-OL TO KILL BACTERIA, YEAST, AND FUNGI

[75] Inventors: Doyle E. Chastain, 137 Birch St., Titusville, Fla. 32780; W. Eugene Sanders; Christine C. Sanders, both of Omaha, Nebr.

[73] Assignee: Doyle E. Chastain, Titusville, Fla.

[21] Appl. No.: 75,788

[22] Filed: Jun. 14, 1993

[51] Int. Cl.5 .................... A01N 31/00; A61K 31/045
[52] U.S. Cl. ............................................. 514/729
[58] Field of Search ........................................ 514/729

[56] References Cited

U.S. PATENT DOCUMENTS 3,743,747  7/1993  Whitehurst .................... 514/729

Primary Examiner—Allen J. Robinson
Attorney, Agent, or Firm—Arthur G. Yeager; Earl L. Tyner

[57] ABSTRACT

MENTH-1-EN-9-OL kills bacteria, yeasts, and fungi by lysing the cell membrane of the organism.

4 Claims, No Drawings

USING MENTH-1-EN-9-OL TO KILL BACTERIA, YEAST, AND FUNGI

TECHNICAL FIELD

The object of this invention is to demonstrate a method of using MENTH-1-EN-9-OL to kill bacteria, yeast, and fungi.

BACKGROUND OF THE INVENTION (1) Field of the invention

During the study of limonene as a hand cleaner, it was found that fully oxygenated limonene can be made bactericidal and fungicidal as was illustrated by the applicants in U.S. Pat. No. 5,153,229. A review of the literature revealed that oxygenated limonene contains several oxidation products including cis and trans-carveol, trans-p-menth-8-ene-1,2-diol, limonene 1,2-epoxide, limonene 8,9-epoxide, cis and trans-p-mentha-2,8-dien-1-ol, and perillyl alcohol, as was outlined by Blumann in Chemical Abstracts, Volume 63, 1965, on page 1819. Because limonene is not bactericidal and because the chemical structures of limonene and perillyl alcohol are identical except for a hydroxyl group replacing a hydrogen atom at carbon 7, the applicants were surprised to find that perillyl alcohol is bactericidal as was shown in U.S. Pat. No. 5,110,832. A review of the terpenes showed that all the monocyclic monoterpenes that are known to be antimicrobial have an oxygen molecule or hydroxyl group replacing a hydrogen atom at carbons 2, 3, 4, or 8. Prior to the discovery that perillyl alcohol is a bactericide, no monocyclic monoterpene with an oxygen or a hydroxyl group at carbon 7, 9 or 10 was recognized as an antimicrobial compound. After the discovery that perillyl alcohol is a bactericide, the applicants decided to study menth-1-en-9-ol (which has a hydroxyl group at carbon 9) for antimicrobial activity and were pleasantly surprised to find that menth-1-en-9-ol kills bacteria, yeast, and fungi in bactericidal and fungicidal concentrations. The chemical structures of limonene and menth-1-en-9-ol follow below.

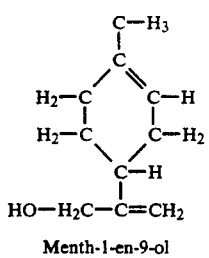

Menth-1-en-9-ol

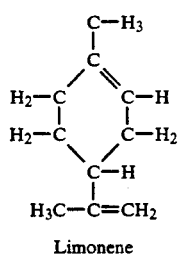

Limonene

Because limonene is not bactericidal and because the chemical structures of limonene and menth-1-en-9-ol are identical except for a hydroxyl group replacing a hydrogen atom at carbon 9, menth-1-en-9-ol was not expected to be bactericidal. It should be noted in the structures of the monocyclic monoterpenes that follow, that none of the monocyclic monoterpenes that are known to be bactericidal, have an oxygen atom or a hydroxyl group at carbon 9 or 10 as can be appreciated in the structures of: perillyl alcohol, carveol, carvone, hydrocarveol, hydrocarvone, pulegone, isopulegol, menthol, menthone, terpinen-4-ol, and a-terpineol which follow.

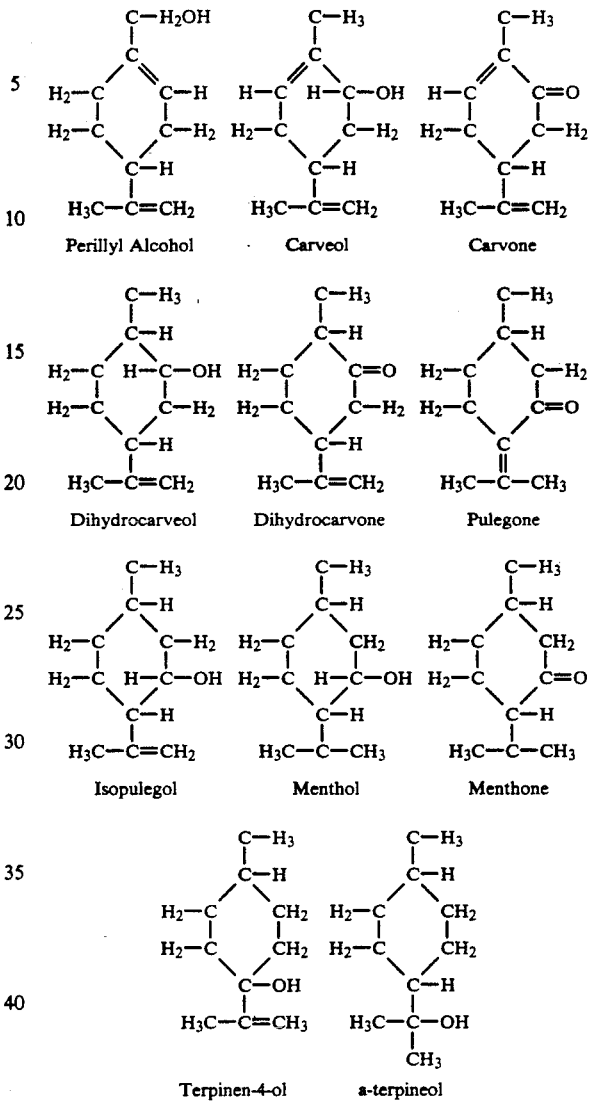

Because it was not expected, the applicants were surprised to find that menth-1-en-9-ol is bactericidal and fungicidal.

Menth-1-en-9-ol is an oil with a fruity aroma. It is insoluble in water, is poorly soluble in propylene glycol, and is almost insoluble in glycerine. Menth-1-en-9-ol is soluble in alcohol and is miscible in oil. It is a naturally occurring oil, but heretofore, it has not been used as a bactericide and fungicide.

As described by Khanna, Vijay and Ladwa, P. H. in the *Indian Journal of Chemistry*, Section B 1987, 26B (9), 816–822, menth-1-en-9-ol can be produced by the hydroboration - oxidation of carvone.

(2) Description of the Prior Art

Zuckerman studied the effect of auto-oxidized d-limonene on bacteria, but found it was weakly bacteriostatic, was unstable, and lost its bacteriostatic effect on keeping as was discussed in Nature 168: 517 (1961). He never studied menth-1-en-9-ol. Kurita investigated the fungicidal activity of several components of essential oils as was reported in Biol. Chem.,45(4), 945–952, 1981, but he never studied the bactericidal nor fungicidal activity of menth-1-en-9-ol against bacteria, yeast nor fungi. Murdock and Allen showed that the germicidal effect of sodium benzoate against yeast was enhanced by orange peel oil and d-limonene, as was outlined in Food Technology Vol 14, No 9, 1960, pages 441–5. They never studied the activity of menth-1-en-9-ol against bacteria, yeast nor fungi. Kellner et al demonstrated that ethereal oils and some of the compounds in the oils have anti-bacterial activity as was reported in Arneimittel-Forechung, 5, 224–9, 1955. He confirmed that limonene is not bactericidal. He never studied menth-1-en-9-ol for bactericidal nor fungicidal activity. Gauvreau showed a means of producing disinfecting compositions in U.S. Pat. No. 3,595,975 by combining cetyl pyridinium with terpenes to form antiseptics, but he never studied menth-1-en-9-ol alone nor in combination with cetyl pyridinium hydrochloride. A. Morel revealed the sterilizing action of carveol, dihydrocarveol, and their ozonization products in Comp. Rend. Soc. Biol. Volume 115, pages 536–8 (1934). He demonstrated the bactericidal effect of carveol and dihydrocarveol, but he never studied the bactericidal nor fungicidal activity of menth-1-en-9-ol.

It should be pointed out that drugs which are bactericidal are usually not fungicidal, and drugs which are fungicidal are usually not bactericidal. In addition, drugs which are bactericidal frequently promote the growth of yeast. Table A, which follows, exemplifies the bactericidal and fungicidal activity of several commonly used antibacterial, antiyeast, and antifungal antibiotics.

TABLE A

| ANTIBIOTICS | ANTIBIOTIC ACTIVITY AGAINST | | | | |
|---|---|---|---|---|---|
| | $Gm^+$ Bac | $Gm^-$ Bac | AFBact | Yeast | Fungi |
| A. ANTIBACTERIAL | | | | | |
| 1. Ampicillin | YES | YES | NO | NO | NO |
| 2. Cephlothin | YES | YES | NO | NO | NO |
| 3. Chloramphenicol | YES | YES | NO | NO | NO |
| 4. Erythromycin | YES | NO | NO | NO | NO |
| 5. Ethambutol | NO | NO | YES | NO | NO |
| 6. Gentamicin | YES | YES | NO | NO | NO |
| 7. Isoniazid | NO | NO | YES | NO | NO |
| 8. Nitrofurantoin | NO | YES | NO | NO | NO |
| 9. Penicillin | YES | NO | NO | NO | NO |
| 10. Rifampin | YES | NO | YES | NO | NO |
| 11. Streptomycin | YES | YES | YES | NO | NO |
| 12. Sulfonamides | NO | YES | NO | NO | NO |
| 13. Tetracycline | YES | YES | NO | NO | NO |
| 14. Vancomycin | YES | YES | NO | NO | NO |
| B. ANTIYEAST | | | | | |
| 1. Nystatin | NO | NO | NO | YES | NO |
| 2. Gentian violet | NO | NO | NO | YES | NO |
| C. ANTIFUNGAL | | | | | |
| 1. Chlotrimazole | NO | NO | NO | YES | YES |
| 2. Griseofulvin | NO | NO | NO | NO | YES |

$Gm^+$ Bac = Gram Positive Bacteria, $Gm^-$ Bac = Gram Negative Bacteria, AFBac = Acid Fast Bacteria, YES = Kills Organism, NO = No Activity Against Organism It should be noted from the table above that none of the anti-bacterial antibiotics kill yeast nor fungi, and none of the anti-yeast nor anti-fungal antibiotics kill bacteria. Thus, an anti-fungal or anti-yeast antibiotic is not expected to kill bacteria and an anti-bacterial antibiotic is not expected to kill yeast nor fungi. Anti-fungal antibiotics do not necessarily kill yeast and anti-yeast antibiotics do not necessarily kill fungi.

DISCLOSURE OF THE INVENTION

This invention relates to the use of menth-1-en-9-ol as a bactericide and fungicide. Menth-1-en-9-ol is an oil which is available commercially, but heretofore, it has not been recognized as a bactericide and fungicide. It is sightly viscous and when applied, readily adheres to glass, metal, wood, cloth, rope, book covers, paper, paint, cement, ceramics, plastic, plant surfaces, skin, mucous membranes, and teeth leaving an oily film. Because it is not soluble in water, its adherence to surfaces allows prolonged exposure and makes menth-1-en-9-ol an ideal bactericide and fungicide regardless of whether they infect plants, animals or humans.

The exact method of killing bacteria, yeast, and fungi is unknown, but it is thought that menth-1-en-9-ol kills bacteria, yeast, and fungi by lysing the cell membrane of the organisms which is lethal to the organisms.

In practice, any surface, on which it is desirable to kill or prevent the growth of bacteria, yeast and fungi, is treated with bactericidal and/or fungicidal concentrations of menth-1-en-9-ol by swabbing, wiping, painting, washing, brushing, spraying, or any other direct application technique. Alternatively, menth-1-en-9-ol can be incorporated in creams, ointments, tinctures, gels, suppositories, paints, sprays, aerosols, toothpastes, solutions, emulsions, soaps, scrubs, mouthwashes, or antiseptic, and applied anywhere it is desirable to kill or prevent the growth of bacteria, yeast, and fungi.

BEST MODE FOR CARRYING OUT THE INVENTION

The following examples are illustrative of the best mode of carrying out the invention. They are, obviously, not to be construed as limitative of the invention since various other embodiments can readily be evolved in view of the teachings provided herein.

EXAMPLE 1

BACTERICIDAL ACTIVITY OF MENTH-1-EN-9-OL AGAINST BACTERIA, YEAST, AND FUNGI

The BACTERICIDE AND FUNGICIDE contemplated by this invention is MENTH-1-EN-9-OL which was studied for bactericidal and fungicidal activity. The organisms tested included the bacteria: *Staphylococcus aureus* ATCC 25923, *Streptococcus mutans* which causes dental plaque, *Escherichera coli* 7, *Salmonella* 14 (para B), *Pseudomonas aeriginosa* 115, the yeast *Candida albicans*, a common cause of skin, mouth, and vaginal infections and the fungi *Cladosporium cladosporides*, and *Aueroblasidium pullans*. The minimal bactericidal and fungicidal concentration of menth-1-en-9-ol needed to kill these bacteria, yeast, and fungi is outlined in Table B below. The menth-1-en-9-ol used in the tests was obtained from Aldrich Chemical Company, Milwaukee, Wis., Catalogue Number 18,374-1 and Lot Numbers 13835-30-8 (01130DT AW) and 18479-69-0 (01130DT EZ)

TABLE B

| BACTERICIDAL AND FUNGICIDAL ACTIVITY OF MENTH-1-EN-9-OL | | | |
|---|---|---|---|
| | MINIMAL BACTERICIDAL CONCENTRATION | | |
| ORGANISM | 10 Min | 60 Min | 24 Hrs |
| A. BACTERIA | | | |
| 1. *Staphylococcus aureus*, | 0.06 | 0.06 | 0.0025 |

TABLE B-continued

BACTERICIDAL AND FUNGICIDAL ACTIVITY OF MENTH-1-EN-9-OL

| ORGANISM | MINIMAL BACTERICIDAL CONCENTRATION | | |
|---|---|---|---|
| | 10 Min | 60 Min | 24 Hrs |
| ATCC 25923 | | | |
| 2. Strepotococcus mutans | 0.10 | 0.005 | 0.0012 |
| 3. Escherichera coli 7 | 0.06 | 0.005 | 0.005 |
| 4. Salmonella 14 (para B) | 0.01 | 0.005 | 0.0025 |
| 5. Pseudomonas aeruginosa ATCC 115 | >0.5 | >0.5 | >0.5 |
| B. YEAST | | | |
| 1. Candida albicans | 0.02 | 0.01 | 0.0025 |
| C. FUNGI | | | |
| 1. Cladosporium cladosporides OM489 | 0.005 | 0.0025 | 0.0025 |
| 2. Aureoblasidium pullans OM279C | 0.005 | 0.0025 | 0.0025 |

The standard assay used to test the bactericidal activity of menth-1-en-9-ol against the different strains of bacteria and yeast was as follows: various dilutions of menth-1-en-9-ol were prepared in an appropriate broth medium for each test strain. An inoculum of $10^6$ colony-forming units (CFU)/ml was used. Each test was incubated at the proper temperature for each organism and subcultured (0.01 ml) at 10 minutes, 60 minutes, and 24 hours onto agar media free of menth-1-en-9-ol. Results were expressed as the bactericidal concentration, i.e. the lowest concentration of menth-1-en-9-ol (ml. menth-1-en-9-ol/total ml of test) killing at least 99.99% of the bacterial inoculum.

TABLE C

Test conditions used to assay the bactericidal activity of menth-1-en-9-ol:

| ORGANISM | BROTH MEDIUM | SUB-CULTURE AGAR MEDIUM | INCUBATION CONDITIONS |
|---|---|---|---|
| 1. Stahylococcus, Enterobacteriacea, and Pseudomonas | Mueller-Hinton | 5% sheep blood | Air @ 37° C. |
| 2. Streptococcus | Todd-Hewitt | 5% sheep blood | 10% $CO_2$ in air at 37° C. |
| 3. Yeast | Sabouraud dextrose | 5% sheep blood | air at 37° C. |
| 4. Fungi | Sabouraud dextrose with 0.05% yeast extract | | air at 37° C. |

EXAMPLE 2

FORMULATIONS WHICH INCORPORATE MENTH-1-EN-9-OL AS A COMPOUND TO KILL BACTERIA, YEAST, AND FUNGI

The following formulations are prepared using menth-1-en-9ol in liquids, gels, soaps, pastes, creams, ointments, suppositories, tampons, aerosols, paints, and emulsions. When bacteria, yeast, and fungi are treated with menth-1-en-9-ol. containing formulations, the formulations kill or prevent the growth of bacteria, yeast, and fungi.

| CHEMICAL | % OF TOTAL | RANGE | ACTION |
|---|---|---|---|
| A. LIQUIDS | | | |
| 1. SOLUTIONS OR SPRAYS | | | |
| a. Menth-1-en-9-ol | 5.0% | 0.1–50% | fungicide |
| Corn Oil | 95.0% | 50–99.9% | diluent |
| | 100.0% | | |
| b. Menth-1-en-9-ol | 1.0% | 0.1–50% | bactericide |
| Ethyl Alcohol | 99.0% | 50–99.9% | diluent |
| | 100.0% | | |
| 2. MOUTHWASH | | | |
| a. Menth-1-en-9-ol | 50.0% | 0.1–50% | antiyeast |
| Flavor | 2.0% | 1–5% | flavor |
| Ethyl Alcohol | 48.0% | 45–98.9% | diluent |
| | 100.0% | | |
| B. DENTIFRICE | | | |
| 1. LIQUID | | | |
| Liquid soap concentrate | 5.0% | 2–10% | surfactant |
| Saccharin | 0.2% | 0.1–1.0% | flavor |
| Clove Oil | 1.0% | 0.5–3.0% | flavor |
| Cinnamon Oil | 0.5% | 0.5–3.0% | flavor |
| Peppermint Oil | 0.5% | 0.5–3.0% | flavor |
| Ethyl Alcohol | 42.6% | 29.5–95.3% | diluent |
| Color | 0.2% | 0.1–0.5% | color |
| Menth-1-en-9-ol | 50.0% | 1–50% | bactericide |
| | 100.0% | | |
| 2. GEL | | | |
| Sodium monofluorophosphate | 0.8% | 0.5–1.5% | antiplaque |
| Menth-1-en-9-ol | 50.0% | 1–50% | bactericide |
| Hydrated silica xerogel | 10.0% | 8–15% | abrasive |
| Hydrated thickening silica | 8.5% | 5–10% | binder |
| Sorbitol 70% solution | 18.8% | 5–73.3% | humectant |
| Polyethylene glycol 32 | 5.0% | 3–7% | bodying agent |
| Sodium lauryl sulfate | 1.5% | 1–2% | surfactant |
| Carboxymethyl cellulose gum | 1.0% | 0.5–2% | binder |
| S D alcohol | 1.0% | 0.5–2% | stabilizer |
| Flavor | 3.0% | 2–4% | flavor |
| Saccharin | 0.2% | 0.1–0.5% | flavor |
| F D & C Green #3 | 0.1% | 0.1–0.5% | color |
| F D & C Yellow #10 | 0.1% | 0.1–0.5% | color |
| | 100.0% | | |
| 3. PASTE | | | |
| Sodium monofluorophosphate | 0.8% | 0.5–1.5% | antiplaque |
| Menth-1-en-9-ol | 50.0% | 1–50% | bactericide |
| Dicalcium phosphate dihydrate | 22.0% | 20.4–30% | abrasive |
| Water | 16.0% | 11.1–69.5% | diluent |
| Glycerine | 5.1% | 4.5–12.5% | bodying agent |
| Flavor | 2.0% | 2–3% | flavor |
| Sodium lauryl sulfate | 1.5% | 1–2% | surfactant |
| Carboxymethyl cellulose gum | 1.4% | 0.5–2.0% | binder |
| Tetrasodium pyrophosphate | 1.0% | 0.5–2.0% | binder |
| Sodium saccharin | 0.2% | 0.1–0.5% | flavor |
| | 100.0% | | |
| C. OINTMENTS & SUPPOSITORIES WITH AND WITHOUT HYDROCORTISONE | | | |
| 1. OINTMENT WITH HYDROCORTISONE | | | |
| Menth-1-en-9-ol | 1.0% | 0.1–15.0% | bacteri- |

-continued

| CHEMICAL | % OF TOTAL | RANGE | ACTION |
|---|---|---|---|
| Polyethylene glycol 3350 | 59.5% | 48.5-59.7% | bodying agent & emulsifier |
| Polyethylene glycol 400 | 39.5% | 31.5-39.7% | bodying agent & emulsifier |
| Hydrocortisone | 1.0%  100.0% | 0.5-5.0% | anti-inflammatory |

2. OINTMENT WITHOUT HYDROCORTISONE

| CHEMICAL | % OF TOTAL | RANGE | ACTION |
|---|---|---|---|
| Menth-1-en-9-ol | 1.0% | 0.1-15.0% | anti-yeast |
| Polyethylene glycol 3350 | 59.5 | 51.0-59.95% | bodying agent & emulsifier |
| Polyethylene glycol 400 | 39.5% 100.0% | 34.0-39.95% | bodying agent & emulsifier |

3. SUPPOSITORY WITHOUT HYDROCORTISONE

| CHEMICAL | % OF TOTAL | RANGE | ACTION |
|---|---|---|---|
| Menth-1-en-9-ol | 1.0% | 0.1-15% | fungicide |
| Polyethylene glycol 1000 | 9.5% | 51.0-59.95% | bodying agent & emulsifier |
| Polyethylene glycol 3350 | 39.5% 100.0% | 34.0-39.95% | bodying agent & emulsifier |

4. SUPPOSITORY WITH HYDROCORTISONE

| CHEMICAL | % OF TOTAL | RANGE | ACTION |
|---|---|---|---|
| Menth-1-en-9-ol | 1.0% | 0.1-15% | anti-yeast |
| Polyethylene glycol 1000 | 74.0% | 60.0-75.2% | bodying agent & emulsifier |
| Polyethylene glycol 3350 | 24.0% | 20.0-24.2% | bodying agent & emulsifier |
| Hydrocortisone | 1.0% 100.0% | 0.5-5.0% | anti-inflammatory |

D. CREAMS WITHOUT HYDROCORTISONE

| CHEMICAL | % OF TOTAL | RANGE | ACTION |
|---|---|---|---|
| Menth-1-en-9-ol | 1.0% | 0.1-15.0% | bactericide |
| Cetyl alcohol | 15.0% | 12.0-18.0% | thickener |
| Arlacel 165** | 5.0% | 3.5-7.5% | emulsifier |
| Sorbitol 70% solution | 5.0% | 3.5-8.0% | humectant |
| Water | 74.5% 100.0% | 51.5-80.9% | diluent |
| Menth-1-en-9-ol | 1.0% | 0.1-15.0% | anti-yeast |
| Spermaceti wax | 12.5% | 10.0-15.0% | thickener |
| Sorbitan monostearate Polyethylene 20 | 10.0% | 7.5-12.5% | emulsifier |
| Sorbitan monostearate | 6.0% | 4.0-8.0% | emulsifier |
| Water | 75.5% 100.0% | 49.5-78.4% | diluent |

E. CREAMS WITH HYDROCORTISONE

| CHEMICAL | % OF TOTAL | RANGE | ACTION |
|---|---|---|---|
| Menth-1-en-9-ol | 1.0% | 0.1-15.0% | anti-yeast |
| Cetyl alcohol | 15.0% | 12.0-18.0% | thickener |
| Arlacel 165** | 5.0% | 3.5-7.5% | emulsifier |
| Sorbitol 70% solution | 5.0% | 3.5-8.0% | humectant |
| Hydrocortisone | 1.0% | 0.5-5.0% | anti-inflammatory |
| Water | 73.0% 100.0% | 46.5-80.4% | diluent |

F. TAMPONS

| CHEMICAL | % OF TOTAL | RANGE | ACTION |
|---|---|---|---|
| Menth-1-en-9-ol (2 cc) 2 Gm | 8.0% | 1-15% | bactericide |
| Tampon 23 Gm | 92.0% 100.0% | 85-99% | reservoir for bactericide |

G. AEROSOLS WITHOUT HYDROCORTISONE

| CHEMICAL | % OF TOTAL | RANGE | ACTION |
|---|---|---|---|
| (1) Menth-1-en-9-ol | 5.0% | 0.5-50% | fungicide |
| Ethyl alcohol | 95.0% 100.0% | 50-99.5% | diluent |

Pressurized nitrogen propellant at 100-125 psig

| CHEMICAL | % OF TOTAL | RANGE | ACTION |
|---|---|---|---|
| (2) Menth-1-en-9-ol | 10.0% | 0.5-50.0% | anti-yeast |
| Soybean Oil | 90.0% 100.0% | 50.0-99.5% | diluent |

Pressurized nitrogen propellant at 100-125 psig

H. AEROSOL WITH HYDROCORTISONE

| CHEMICAL | % OF TOTAL | RANGE | ACTION |
|---|---|---|---|
| Menth-1-en-9-ol | 10.0% | 0.5-50% | bactericide |
| Soybean oil | 98.0% | 45-99.0% | diluent |
| Hydrocortisone | 1.0% 100.0% | 0.5-5.0% | anti-inflammatory |

Pressurized nitrogen propellant at 100-125 psig

I. OIL IN WATER EMULSION

| CHEMICAL | % OF TOTAL | RANGE | ACTION |
|---|---|---|---|
| (1) Menth-1-en-9-ol | 0.1% | 0.1-50% | fungicide |
| (2) Corn oil | 10.0% | 10-15% | oil |
| (2) Arlacel 40** | 2.0% | 1-3% | emulsifier |
| (2) Tween 40 | 3.0% | 2-4% | emulsifier |
| (3) Water | 84.9% 100.0% | 28-86.9% | diluent |

Heat (2) to 70° C. Heat (3) to 72° C. Add (3) to (2) with continuous agitation. When (3) and (2) cool to 40° C., add (1) with continuous agitation until room temperature is reached.

J. OIL IN WATER EMULSION WITH SOAP (FUNGICIDAL OR BACTERICIDAL SOAP)

| CHEMICAL | % OF TOTAL | RANGE | ACTION |
|---|---|---|---|
| (1) Menth-1-en-9-ol | 1.0% | 0.1-25% | bactericide |
| (2) Corn oil | 30.0% | 20.0-40.0% | oil |
| (2) Arlacel 40** | 2.0% | 1.0-3.0% | emulsifier |
| (2) Tween 40 | 3.0% | 2.0-4.0% | emulsifier |
| (2) Liquid soap concentrate | 3.5% | 2.5-5.0% | surfactant |
| (3) Water | 60.5% 100.0% | 23-74.4% | diluent |

Heat (2) to 70° C. Heat (3) to 72° C. Add (3) to (2) with continuous agitation. When (3) and (2) cool to 40° C., add (1) with continuous agitation until room temperature is reached.

K. WATER IN OIL EMULSION

| CHEMICAL | % OF TOTAL | RANGE | ACTION |
|---|---|---|---|
| (1) Menth-1-en-9-ol | 1.0% | 0.1-25% | anti-yeast |
| (2) Arlacel 186** | 3.0% | 2.0-4.0% | emulsifier |
| (2) Soybean oil | 15.0% | 10.0-25.0% | oil |
| (2) Ceresin wax | 0.5% | 0.3-0.6% | thickener |
| (2) Beeswax | 0.5% | 0.3-0.6% | thickener |
| (2) Tween 80 | 0.5% | 0.3-0.6% | emulsifier |
| (3) Water | 79.5% 100.0% | 44.2-87.0% | diluent |

| CHEMICAL | % OF TOTAL | RANGE | ACTION |
|---|---|---|---|
| Heat (2) to 70° C. Heat (3) to 72° C. Add (3) to (2) with continuous agitation. When (3) and (2) cool to 40° C., add (1) with continuous agitation until room temperature is reached. | | | |

L. PAINT

1. ENAMEL

| CHEMICAL | % OF TOTAL | RANGE | ACTION |
|---|---|---|---|
| Menth-1-en-9-ol | 1.00% | 1–10% | bactericide |
| Titanium dioxide | 14.91% | 12–16% | pigment |
| Calcium carbonate | 29.83% | 25–35% | pigment |
| Silicate | 4.81% | 3–6% | pigment |
| Soya alkyd resin | 25.72% | 22–28% | pigment (binder) |
| Mineral spirits | 23.73% | 5–37% | solvent (thinner) |
|  | 100.00% | | |

2. LATEX

| CHEMICAL | % OF TOTAL | RANGE | ACTION |
|---|---|---|---|
| Menth-1-en-9-ol | 1.0% | 1–10% | fungicide |
| Titanium dioxide | 10.76% | 8–12% | pigment |
| Silicate | 12.91% | 10–16% | pigment |
| Calcium carbonate | 20.91% | 15–25% | pigment |
| Vinyl acrylic resin solids | 12.22% | 10–16% | vehicle (binder) |
| Glycol | 8.30% | 6–10% | solvent (thinner) |
| Water | 34.00% | 12–50% | solvent (thinner) |
|  | 100.00% | | |

*Croda, Inc., 51 Madison Ave., New York, New York 10010
**Glycerol monostearate and polyoxyethylene stearate ICI of America (Formerly Atlas Chemical Industries), Wilmington, Delaware 19899

While only certain preferred embodiments of this invention have been shown and described by way of illustration, many modifications will occur to those skilled in the art and it is, therefore, desired that it be understood that it is intended herein, to cover all such modifications that fall within the true spirit and scope of this invention.

What is claimed and what is intended to be secured by Letters Patent of the United States is:

1. A method of killing bacteria and fungi comprising treating bacteria and fungi in their habitat with bactericidal and fungicidal concentrations of menth-1-en-9-ol.

2. The method of claim 1 wherein said bacteria are selected from a group consisting of Staphylococcus, Enterobacteriaceae, and Streptococcus.

3. The method of claim 1 wherein said fungi are selected from a group consisting of Aureoblasidium and Cladosporium.

4. A method of killing yeast consisting of treating yeast in their habitat with effective concentrations of menth-1-en-9-ol to kill said yeast.

* * * * *